US00PP21561P2

(12) United States Plant Patent
Ranney

(10) Patent No.: US PP21,561 P2
(45) Date of Patent: Dec. 7, 2010

(54) ***CLETHRA ALNIFOLIA* PLANT NAMED "CRYSTALINA"**

(50) Latin Name: *Clethra alnifolia*
Varietal Denomination: Crystalina

(75) Inventor: Thomas G. Ranney, Arden, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 12/587,761

(22) Filed: Oct. 13, 2009

(51) Int. Cl.
*A01H 5/00* (2006.01)

(52) U.S. Cl. ..... Plt./226

(58) Field of Classification Search ..... Plt./226, Plt./263.1

See application file for complete search history.

*Primary Examiner*—Annette H Para
(74) *Attorney, Agent, or Firm*—Jondle & Associates, P.C.

(57) ABSTRACT

'Crystalina' is a new variety of *Clethra alnifolia* with a low, compact, rounded habit, with long flower racemes and numerous fragrant flowers, is disclosed.

2 Drawing Sheets

Genus and species: *Clethra alnifolia.*
Variety denomination: 'Crystalina'.

BACKGROUND OF THE INVENTION

The present invention comprises a new and distinct cultivar of summersweet plant, botanically known as *Clethra alnifolia*, and hereinafter referred to by the cultivar name 'Crystalina'. This new summersweet was developed through a breeding program at North Carolina State University, Mills River, N.C. 'Crystalina' was selected from a population of approximately 1,500 open pollinated seedlings from *Clethra alnifolia* 'Ruby Spice' (unpatented) in 2003. Seeds from the open pollination were collected in 2003 and selections were first made in 2006.

The first asexual propagation of 'Crystalina' was carried out in August 2006 by rooting stem cuttings in Mills River, N.C. and has been asexually reproduced repeatedly by vegetative cuttings in North Carolina over a 3 year period. 'Crystalina' roots readily from softwood cuttings treated with a basal dip of 4,000 ppm indole butyric acid (potassium salt) in water. 'Crystalina' has been found to retain its distinctive characteristics through successive asexual propagations via vegetative cuttings.

REFERERENCE TO PLANT BREEDER'S RIGHTS

Plant Breeder's Rights for this cultivar have been applied for in Canada on Sep. 17, 2009. 'Crystalina' has not been made publicly available more than one year prior to the filing date of this application.

SUMMARY OF THE INVENTION

The following are the most outstanding and distinguishing characteristics of this new cultivar when grown under standard horticultural practices in Mills River, N.C.

1. Compact, rounded growth habit;
2. Long flower racemes; and
3. Numerous flowers per raceme.

DESCRIPTION OF THE PHOTOGRAPHS

This new summersweet plant is illustrated by the accompanying photographs which show the plant's form, foliage and inflorescences. The colors shown are as true as can be reasonably obtained by conventional photographic procedures.

DESCRIPTION OF THE NEW VARIETY

Figure 1:
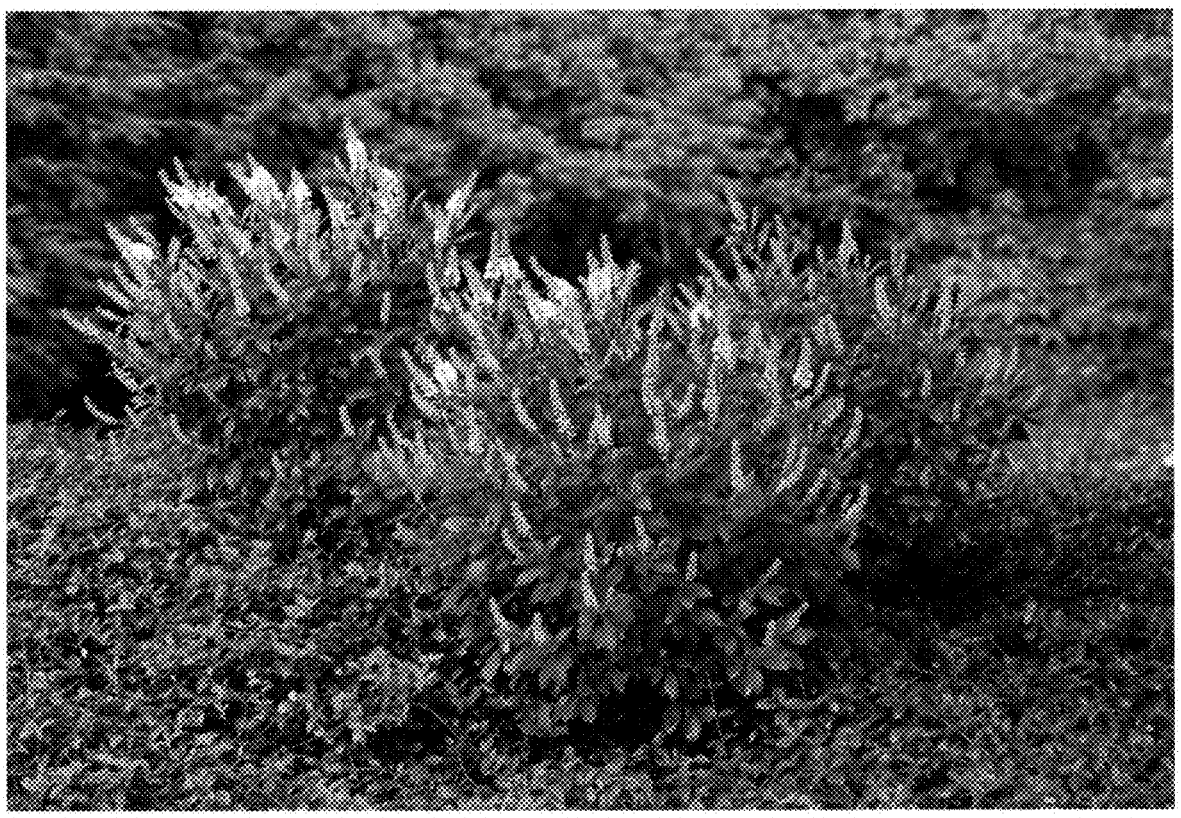
FIG. 1 shows a 3-year-old plant growing in landscape conditions in Arden, N.C. in July, 2009.
Figure 2:
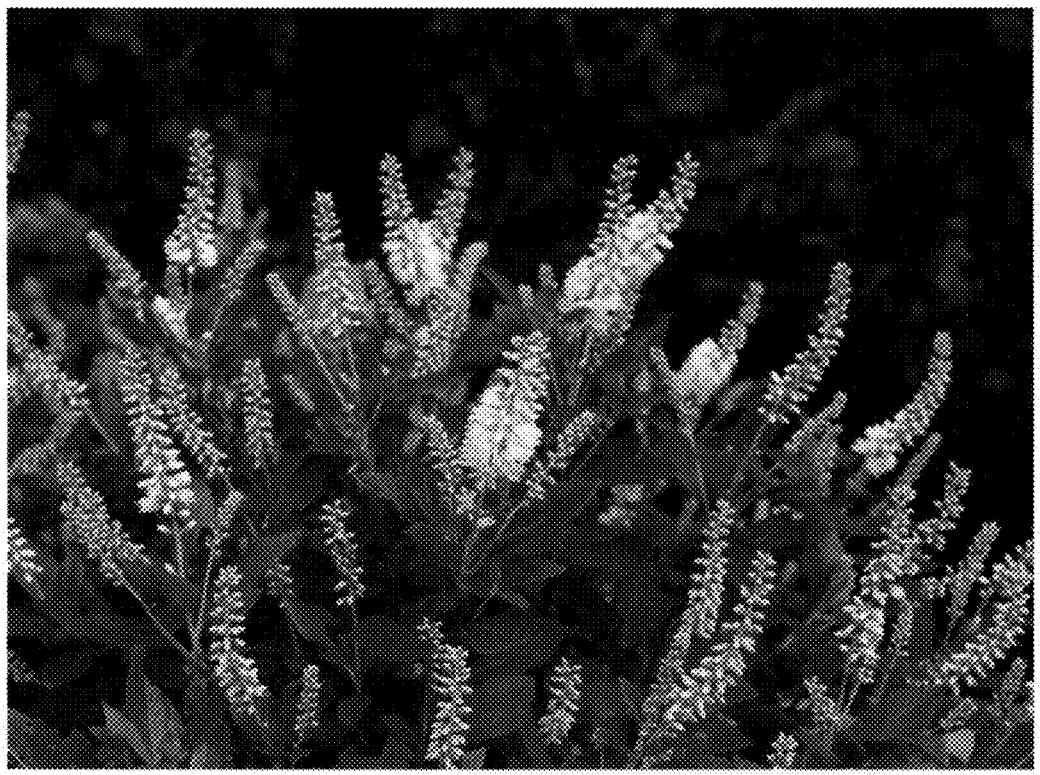
FIG. 2 shows details of the flowers and inflorescence in Arden, N.C. in July 2009.
Figure 3:
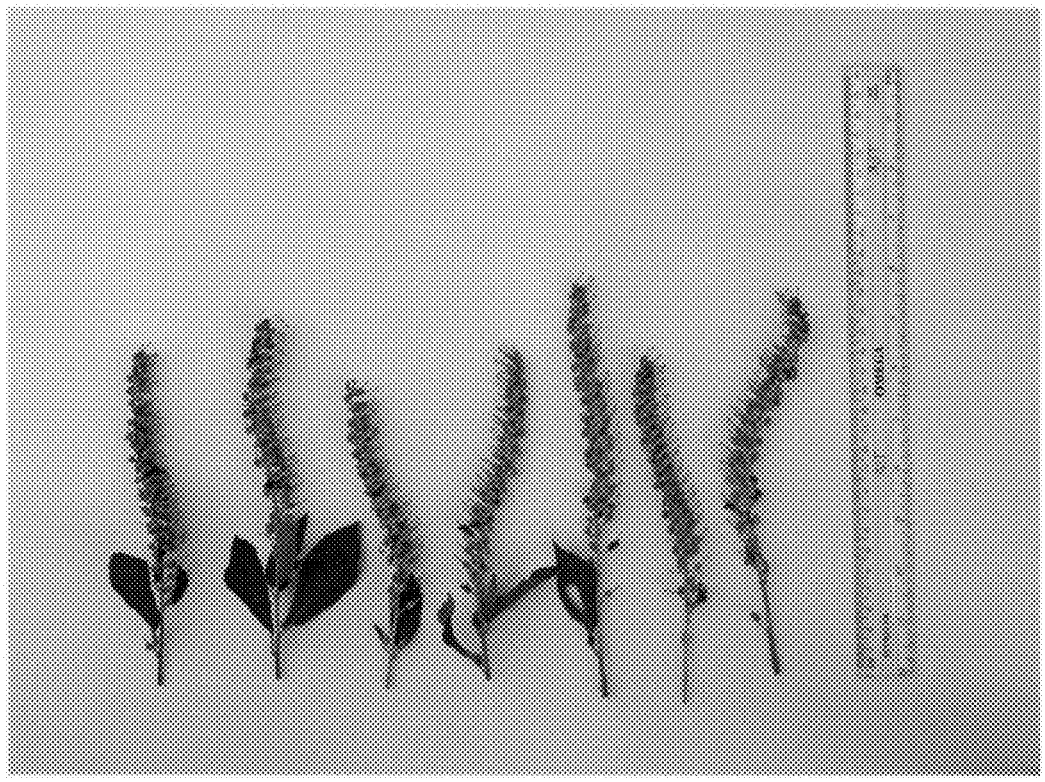
FIG. 3 shows details of the long inflorescence racemes in Arden, N.C. in July 2009.

The following detailed description sets forth the distinctive characteristics of 'Crystalina'. The detailed description was taken on 5-year-old plants growing under landscape conditions in Mills River, N.C. in July 2009. Color references are to The R.H.S. Colour Chart of The Royal Horticultural Society of London (R.H.S.), 2001 Edition.

DETAILED BOTANICAL DESCRIPTION

Classification:
- *Botanical name.*—*Clethra alnifolia.*
- *Common name.*—Summersweet.
- *Variety name.*—'Crystalina'.

Parentage: Open pollination of seedlings of *Clethra alnifolia* 'Ruby Spice' (unpatented).

Plant description:
- *Growth habit.*—Low, compact, and slightly spreading.
- *Plant shape.*—Rounded to slightly spreading.
- *Height at maturity.*—0.8 meters to 1.2 meters.
- *Width at maturity.*—1.2 meters to 1.5 meters.

Stem:
- *Mature stem texture.*—Slight stellate pubescence.
- *Mature stem color.*—Closest to RHS N199C (Greyed-Brown).
- *Immature stem texture.*—Slight stellate pubescensce.
- *Immature stem color.*—RHS N144 (Yellow-Green).

Leaves:

*Type.*—Deciduous.

*Arrangement.*—Alternate.

*Shape.*—Simple, elliptic to oblanceolate.

*Apex.*—Acuminate.

*Veins.*—Upper (Adaxial) surface: Ribbed, reticulate, pinnate. Lower (Abaxial) surface: Midvein and laterals impressed.

*Mature leaf texture.*—Mostly glabrous; slight pubescence, sometimes stellate, confined to the veins both upper and lower surface.

*Base.*—Cuneate.

*Margin.*—Serrate for three quarters or more of the distance from apex to the base with the remainder entire.

*Mature leaf size.*—Length: Average is 8.4 cm (range is 7.5 cm to 9.6 cm). Width at widest: Average is 3.5 cm (range is 3.1 cm to 3.7 cm).

*Immature leaf color.*—Adaxial (upper) surface: Tending to be either RHS 137A (Green) or RHS 143A (Green). Adaxial (upper) vein: RHS 152D (Yellow-Green). Abaxial (lower) surface: RHS 144B (Green). Abaxial (lower) vein: RHS 144C (Yellow-Green).

*Immature leaf texture.*—Adaxial surface texture: Slight stellate pubescence. Abaxial surface texture: Midrib pubescent, the rest of the surface with slight stellate pubescence.

*Mature leaf color.*—Adaxial (upper) surface: Closest to RHS 139A (Green). Adaxial (upper) vein: RHS 152D (Yellow-Green). Abaxial (lower) surface: Either RHS 146B (Yellow-Green) or RHS 146A (Yellow-Green). Abaxial (lower) vein: Midvein RHS 145C (Yellow-Green).

*Fall foliage color.*—RHS 11 (Yellow).

*Leaf attachment.*—Petiolate.

*Petiole.*—Shape: Semi-terete. Length: Average is 11.1 mm (range is 9.5 mm to 13.8 mm). Width: Average is 1.4 mm (range is 1.3 mm to 1.5 mm). Surface: Pubescent.

Inflorescence:

*Number of flowers per inflorescence.*—65 to 90 on the main, terminal shoot, raceme with 30 to 60 on the lateral, side racemes.

*Type.*—Racemes.

*Habit.*—Upright.

*Flowering season.*—Seasonal (summer), June to July, over a 4 to 6 week period.

*Lastingness of flower on the plant.*—2 to 5 days per flower with individual racemes blooming over 7 to 21 days.

*Fragrance.*—Sweet spicy.

*Length at anthesis.*—Average terminal raceme is 15.5 cm (range is 11 cm to 20.0 cm).

*Self cleaning or persistent.*—Persistent raceme.

*Bud.*—Distal bud shape: Ovoid. Distal bud diameter: Average 2.4 mm (range is 2.2 mm to 2.6 mm). Distal bud length: Average 4.8 mm (range is 3.9 mm to 5.7 mm). Proximal (prior to petal opening) shape: Ovoid. Proximal (prior to petal opening) diameter: Average 2.8 mm (range is 2.7 mm to 2.9 mm). Proximal (prior to petal opening) length: Average 6.5 mm (range is 6.2 mm to 6.8 mm).

*Perianth.*—Diameter at antithesis: Average 11.5 mm (range is 10 mm to 13 mm).

*Petal.*—Number of petals per flower: Five. Color, adaxial (upper) surface at anthesis: RHS 155C (White). Color, abaxial (lower) surfaces at anthesis: RHS 144C (White). Surface texture and appearance: Glabrous and lustrous. Shape: Obovate. Apex: Recuse. Base: Truncate. Margin: Entire. Length: Average is 6 mm (range is 5.8 mm to 6.2 mm). Width: Average is 2.5 mm (range is 2.1 mm to 2.8 mm). Petals, fused or unfused: Unfused.

*Pedicel.*—Color: Proximal RHS 144C (Yellow-Green) RHS 154D (Yellow-Green) at the distal end. Length: Average 2.1 mm (range is 1.3 mm to 2.9 mm). Width: Average 0.36 mm (range is 0.26 mm to 0.45 mm).

*Peduncle.*—Shape: Laterally compressed cylinder. Length: Average is 30 mm (range is 16 mm to 44 mm). Width: Average is 1.9 mm (range at the base is 0.9 mm to 2.9 mm) tapering to (range 0.62 mm to 0.78 mm). Color: Closest to RHS 145B (Yellow-Green). Surface texture: Pubescent.

*Bract.*—Number: Single persistent. Length: Average 8.6 mm (range is 3.5 mm to 13.6 mm). Color: Most proximal bract is closest to RHS 139A (Green) while the other bracts are closest to RHS 150B (Yellow-Green).

*Sepals.*—Number: 5. Color: Both adaxial and abaxial surfaces closest to N144A (Yellow-Green). Surface texture: Pubescent. Shape: Lanceolate. Apex: Acute. Base: Truncate. Margin: Entire. Length: Average 4.5 mm (range is 3.3 mm to 5.6 mm). Width: Average 2.0 mm (range is 1.5 mm to 2.4 mm).

Reproductive organs:

*Stamen.*—Quantity per flower: 9 or 10. Shape: Filament. Color: Translucent RHS 155C (White). Length: Average is 7.1 mm (range is 5.9 mm to 8.3 mm). Width: Less than 0.50 mm. Anther: Length: Average is 1.5 mm (range is 1.4 mm to 1.6 mm). Width at widest: Average is 0.8 mm (range is 0.76 mm to 0.84 mm). Color: Mostly RHS 19B (Yellow) but maturing to RHS 172B (Grey-Orange). Pollen color: RHS 4D (Yellow). Attachment: Dorsifixed.

*Pistil.*—Length: Average 6 mm (range 5 mm to 7 mm). Width: Less than 0.5 mm.

*Ovary.*—Superior, tricarpellary syncarpous.

Fruit/seed set:

*Fruit.*—Color: Initially RHS 138C (Light Green) maturing to RHS 177C (Greyed-Orange). Shape: Subglobose. Surface texture: Pubescent. Size: 2 mm to 4 mm wide and 3 mm to 5 mm long. Amount of fruit set: Copious.

*Seed.*—Color: 166B (Greyed-Orange). Shape: Flat. Diameter: 1 mm to 2 mm.

Disease and insect resistance: No significant disease or insect pests have been observed.

COMPARISON WITH PARENTAL LINE AND KNOWN VARIETY

Table 1 shows the differences between 'Crystalina' and the commercial variety 'Solite' (U.S. Plant Pat. No. 15,505) and the female parent 'Ruby Spice' (unpatented).

As shown in Table 1, 'Crystalina' is distinguished from the female parent, *Clethra alnifolia* 'Ruby Spice' (unpatented) in that 'Crystalina' has white flowers, while 'Ruby Spice' has red flowers. Additionally, 'Crystalina' has a more compact, rounded growth habit than 'Ruby Spice'. 'Crystalina' also has longer racemes with more flowers than either 'Sotite' or 'Ruby Spice'.

TABLE 1

| Comparison to Commercial Varieties | | | |
|---|---|---|---|
| | Variety | | |
| Trait | 'Crystalina' | 'Sotite' | 'Ruby Spice' |
| Flower color | RHS 155C (White) | RHS 155C (White) | Mostly RHS 61B (Red-Purple) with RHS 155C (White) highlights |
| Mature Height | 0.8 m to 1.2 m | 0.6 m to 1.0 m | 2.5 m to 3.6 m |
| Growth habit | Compact, rounded to slightly spreading | Low compact | Large, upright |
| Raceme length | 11 cm to 20 cm | 7 cm to 10 cm | 6 cm to 10 cm |

TABLE 1-continued

| Comparison to Commercial Varieties | | | |
|---|---|---|---|
| | Variety | | |
| Trait | 'Crystalina' | 'Sotite' | 'Ruby Spice' |
| Number of flowers per raceme: Primary | 65 to 90 | 70 to 80 | 30 to 65 |
| Number of flowers per raceme: Secondary | 30 to 60 | 30 to 50 | 8 to 40 |

I claim:

1. A new and distinct cultivar of *Clethra alnifolia* plant as shown and described herein.

* * * * *